United States Patent
Campbell et al.

(10) Patent No.: US 11,085,925 B2
(45) Date of Patent: Aug. 10, 2021

(54) ISOMERIC REAGENT TAGS FOR DIFFERENTIAL MOBILITY SPECTROMETRY

(71) Applicant: DH Technologies Development Pte. Ltd., Singapore (SG)

(72) Inventors: John L. Campbell, Milton (CA); Yves LeBlanc, Newmarket (CA); Chang Liu, Richmond Hill (CA)

(73) Assignee: DH Technologies Development Pte. Ltd., Singapore (SG)

( * ) Notice: Subject to any disclaimer, the term of this patent is extended or adjusted under 35 U.S.C. 154(b) by 393 days.

(21) Appl. No.: 15/779,944

(22) PCT Filed: Nov. 29, 2016

(86) PCT No.: PCT/IB2016/057192
§ 371 (c)(1),
(2) Date: May 30, 2018

(87) PCT Pub. No.: WO2017/093898
PCT Pub. Date: Jun. 8, 2017

(65) Prior Publication Data
US 2018/0328934 A1   Nov. 15, 2018

Related U.S. Application Data

(60) Provisional application No. 62/261,073, filed on Nov. 30, 2015.

(51) Int. Cl.
*G01N 33/00* (2006.01)
*G01N 33/58* (2006.01)
*G01N 27/624* (2021.01)
*G01N 33/68* (2006.01)
*H01J 49/00* (2006.01)

(52) U.S. Cl.
CPC .......... *G01N 33/58* (2013.01); *G01N 27/624* (2013.01); *G01N 33/6848* (2013.01); *H01J 49/0045* (2013.01); *G01N 33/582* (2013.01); *G01N 2458/00* (2013.01)

(58) Field of Classification Search
CPC .. G01N 33/582; G01N 33/58; G01N 33/6848; G01N 27/624; G01N 2458/00; H01J 49/0045
See application file for complete search history.

(56) References Cited

U.S. PATENT DOCUMENTS

| | | | |
|---|---|---|---|
| 2005/0208550 A1 | 9/2005 | Pappin et al. | |
| 2012/0032073 A1 | 2/2012 | Rand et al. | |
| 2013/0184181 A1* | 7/2013 | Purkayastha | G01N 33/58 506/12 |
| 2015/0069227 A1* | 3/2015 | Wu | G01N 27/622 250/282 |
| 2015/0129762 A1 | 5/2015 | Campbell et al. | |

FOREIGN PATENT DOCUMENTS

| | | | |
|---|---|---|---|
| WO | 2004079334 A2 | 9/2004 | |
| WO | WO-2004079334 A2 * | 9/2004 | ........... C12Q 1/6823 |

OTHER PUBLICATIONS

Mie, Axel et al. "Enantiomer separation of amino acids by complexation with chiral reference compounds and high-field asymmetric waveform ion mobility spectrometry: Preliminary results and possible limitations." Analytical Chemistry (2007) 79 2850-2858. (Year: 2007).*
International Search Report and Written Opinion for PCT/IB2016/057192 dated Mar. 8, 2017.

* cited by examiner

*Primary Examiner* — Christopher Adam Hixson

(57) ABSTRACT

Methods and systems for separating and/or quantifying compounds, using differential mobility spectrometry (DMS) are provided herein. In accordance with various aspects of the applicants' teachings, the methods and systems can provide for the quantification of one or more compounds, for example, using isomeric labels that can be less costly to produce relative to conventional tags that incorporate stable-isotope labels. The present teachings can quantify the relative amount of a compound based on the effect of using an easily charged functional group as well as a functional group positioned at a resonant or non-resonant position through a DMS. In some aspects, methods and systems in accordance with various aspects of the present teachings provide for the detection and/or quantification of the analytes labeled with isomeric tags that can be differentiated via a DMS upstream of a first stage mass analyzer and/or prior to fragmentation of the labeled analyte, for example.

6 Claims, 10 Drawing Sheets

2-AP

3-AP

4-AP

EWG (F) in resonance
Large negative CV shift

EWG (F) not in resonance
Moderate negative CV shift

EWG (F) not part of pi system
No negative CV shift

Protonated substituted 2-methyl-quinolin-8-ols

X = -OCH$_3$ -CH$_3$, -F, -Br, or -CN

5-Position

6-Position

7-Position

ISOMERIC REAGENT TAGS FOR DIFFERENTIAL MOBILITY SPECTROMETRY

RELATED APPLICATIONS

This application claims the benefit of priority from U.S. Provisional Application Ser. No. 62/261,073, filed on Nov. 30, 2015, the entire contents of which are incorporated by reference, herein.

FIELD

The present teachings generally relate to methods and systems for the separation or detection of analytes labeled with isomeric reagent tags, and more particularly, to methods and systems utilizing differential mobility spectrometry to separate labeled analytes.

BACKGROUND

The use of isotopically or isobarically labelled derivatives or "tags" to perform relative quantitation in tandem mass spectrometry (MS/MS) based workflows is known. Generally in such techniques, an analyte of interest from each of a plurality of samples can be reacted with an isotopic or isobaric labeling reagent that exhibits a unique mass spectrometric signature when the labeled analytes is subsequently subject to fragmentation (e.g., via collision induced dissociation or CID). After an analyte of interest within multiple samples are labeled with different isotopic or isobaric tags, the samples can then be mixed together and subject to MS/MS-based analysis, with the analytes from each sample ultimately being differentiated based, for example, on the difference in mass of the isotopes present in the labeling reagent or through the release of a unique reporter ion following fragmentation of the labeled analytes. By way of example, isobaric tags for relative and absolute quantitation (iTRAQ) is a known isobaric labeling method used in quantitative proteomics by tandem MS/MS to determine the quantitation of proteins from different samples in a multiplexed experiment. In a typical iTRAQ workflow, the iTRAQ labeling reagents covalently bond to the N-terminus or side chain amines of peptide(s) of interest. These differentially-labeled samples are then pooled, and analyzed by tandem MS/MS, with selective fragmentation of the labeled analyte occurring prior to the second MS stage so as to generate a low molecular mass reporter ion that is detected to identify the peptides and the proteins from which they originated. Tandem mass tags (TMT) are another common isobaric label used for MS-based quantification and identification of biological macromolecules such as proteins, peptides, and nucleic acids. While the chemical structure of the TMTs are identical such that analytes labeled therewith are generally indistinguishable in single MS mode, each tag contains isotopes substituted at various positions such that the mass reporter and mass normalization regions of the tags have different molecular masses that can be distinguished in a second MS stage following fragmentation of the labeled analytes and the release of the tags.

However, both iTRAQ and TMT require the use of expensive reagents, such as costly, stable isotope-labeled precursors. Additionally, it can be difficult to generate pure isotopic labels such that batch-to-batch corrections are required, thereby adding to the complexity of the analysis.

Accordingly, there remains a need for a cost-effective, improved MS-based quantitation and identification of labeled compounds.

SUMMARY

In accordance with various aspects of the applicant's teachings, methods and systems for the separation or detection of analytes labeled with isomeric reagent tags using differential mobility spectrometry are provided herein. Whereas typical MS/MS workflows involving isotopic or isobaric labels rely on the fragmentation of the labeled analyte and release of the tags to allow for MS-based separation/detection of the unique tags, methods in accordance with various aspects of the present teachings provide for the detection and/or quantification of one or more analytes of interest (e.g., peptides, sugars, and glycans) by labeling the analyte(s) with isomeric labeling reagents that enable differential separation of the labeled analytes via a differential mobility spectrometer (DMS) located upstream of a first stage mass analyzer and/or prior to fragmentation of the labeled analyte, for example. The differential labels described herein can include or exclude additional stable-isotope labels, though it will be appreciated in light of the present teachings that their exclusion can reduce the expense and/or complexity of the labeling reagents relative to reagents commonly utilized in known isotopic or isobaric tandem MS-based workflows.

In various aspects of the present teachings, a method of analyzing a plurality of samples is provided comprising separately reacting first and second samples containing or suspected of containing an analyte of with different isomeric labels so as to differentially label the analytes from each sample, thereby generating a plurality of differentially labeled analytes; mixing the differentially labeled analytes; ionizing the mixture of differentially labeled analytes so as to generate ionized labeled analytes; and performing ion mobility spectrometry on the ionized labeled analytes. In some aspects, the method can also comprise performing liquid chromatography (LC) on the mixture of differentially labeled analytes prior to performing ion mobility spectrometry.

In various aspects, the ion mobility spectrometer can be operated so as to selectively transmit one of the plurality of ionized labeled analytes. For example, the ion mobility spectrometry is performed with a differential mobility spectrometer and the method can further comprise adjusting at least one of a compensation voltage and a separation voltage of the differential mobility spectrometer to maximize transmission therethrough of one species of the ionized labeled analytes relative other species of the ionized labeled analytes. Additionally or alternatively in accordance with various aspects of the present teachings, the method can also comprise adding a chemical modifier to a carrier gas of the ion mobility spectrometer to maximize transmission therethrough of one species of the ionized labeled analytes relative other species of the ionized labeled analytes. In some aspects, the method can also comprise performing ion mobility separations on the mixture of differentially labeled analytes using drift-time ion mobility spectrometry, traveling-wave mobility spectrometry, or high-field asymmetric waveform ion mobility spectrometry.

The isomeric labeling reagents can comprise a variety of chemical structures, each of which displays different behaviors in the DMS cell by virtue of their isomeric forms. By way of example, in some aspects, the different isomeric labels can differ in the locations of a given functional group, wherein the functional group is in resonance with the ion's charge site on one species of the isomeric label and is not in resonance on another species of the isomeric label. In some related aspects, the functional group can be an electron donating group or an electron withdrawing group. By way of non-limiting example, the electron donating group is selected from the group consisting of $NH_2$, $OCH_3$, OH, and $CH_3$, and the electron withdrawing group is selected from the group consisting of F, Cl, Br, I, $NO_2$, and CN.

By way of example, in some aspects, the different isomeric labels can differ in the locations of a given functional group, wherein the functional group is involved in intramolecular hydrogen bonding (IMHB) with the ion's charge site on one species of the isomeric label and is not involved in IMHB on another species of the isomeric label. Isomers engaged in IMHB will typically observe lesser degrees of interaction with solvent molecules in a DMS cell compared to non-IMHB isomers, hence the driving force for their separation.

In accordance with various aspects of the present teachings, a kit for analyzing one or more samples containing or suspected of containing an analyte of interest is provided, the kit comprising a plurality of isomeric labels, wherein each of the isomeric labels exhibit differences in chemical structure such that the same analyte labeled with each of the isomeric labels exhibit different differential ion mobility behaviors. For example, the differences in chemical structure can comprise a different location of binding of a functional group, wherein the functional group is in resonance with the ion's charge site on one species of the isomeric label and is not in resonance on another species of the isomeric label. In some related aspects, the functional group can be an electron donating group or an electron withdrawing group. By way of non-limiting example, the electron donating group is selected from the group consisting of $NH_2$, $OCH_3$, OH, and $CH_3$, and the electron withdrawing group is selected from the group consisting of F, Cl, Br, I, $NO_2$, and CN, by way of non-limiting example. In some aspects, the kit can also include labeling reagents for binding the label with the analyte of interest.

In various aspects, the present teachings provide a mixture comprising the same analyte (e.g., a peptide, protein, carbohydrate, lipid, steroid, or a small molecule having a molecular weight less than 1500 daltons) from a plurality of samples labeled with two or more different isomeric labels, wherein differences in the chemical structures of the labels results in different differential ion mobility behaviors for the labeled analytes. In various related aspects, the differential ion mobility behaviors are different amongst the differentially-labeled analytes as a result of electronic and/or steric effects arising from the substitution patterns of the isomeric labels. In some aspects, the isomeric labels can incorporate stable-isotope labels to allow for an expanded set of isomeric labels for DMS analysis.

In some aspects, the present teachings relates to a plurality of isomeric tags for tagging a compound in a sample is described herein. Each of the isomeric tags comprises a chemically reactive moiety configured to bind to and tag the compound in the sample and a site capable of carrying a positive charge or a negative charge.

In some aspects, the plurality of isomeric tags can have a full positive charge or full negative charge. In some aspects, the charge is a partial positive or a partial negative charge.

In some aspects, the plurality of isomeric tags that can be used comprise a functional group at one of a plurality of positions. For example, the functional group can be an electron donating group or an electron withdrawing group. An electron donating group can donate electron density to a π-conjugated system, selected from the group consisting of $NH_2$, $OCH_3$, OH, and $CH_3$, and an electron withdrawing group can remove electron density from a π-conjugated system, selected from the group consisting of F, Cl, Br, I, $NO_2$, and CN, by way of non-limiting example.

As described herein, a group of isomeric tags can all have the same chemical formula yet a functional group substituted at different positions on the tag. In some aspects, the functional group in one isomeric tag can be at a resonant position. In other aspects, the functional group in another isomeric tag can be at a non-resonant position. By way of example, in some aspects, the different isomeric labels can differ in the locations of a given functional group, wherein the functional group is involved in intramolecular hydrogen bonding (IMHB) with the ion's charge site on one species of the isomeric label and is not involved in IMHB on another species of the isomeric label.

In some aspects, a chemical modifier can be added to a transport region in a DMS to effect a shift in the compensation voltage of the tagged compound. By way of non-limiting example, the chemical modifier can comprise, for example, water, methanol, ethanol, isopropyl alcohol, or acetonitrile.

In some aspects, the isomeric tags can chemically react with a compound or group of compounds (e.g., via a chemically reactive moiety) to be detected, separated and/or quantified. For example, the compound to be detected, separated and/or quantified can comprise an amino acid sequence, such as a peptide or protein. The compound can also comprise a sugar or a carbohydrate. For example, a carbohydrate can include monosaccharides, disaccharides, and polysaccharides. Examples of monosaccharides include, but is not limited to glucose, fructose, galactose . . . . Examples of disaccharides and polysaccharides include but is not limited to sucrose, maltose, lactose . . . .

In some aspects, the present teachings relates to a method of analyzing (i.e, detecting, separating, and/or detecting) a compound in a sample. The method comprises reacting the compound with an isomeric tag comprising a chemically reactive moiety, wherein the chemically reactive moiety reacts with and binds to the compound thereby forming a tagged compound. The method further comprises ionizing the tagged compound so as to form a tagged compound ion complex and transporting the tagged compound ion complex through a differential mobility spectrometer with a chemical modifier to effect separation of the tagged compound ion complex, thereby allowing quantification of the compound in the sample.

The isomeric tags described herein comprise a functional group. In some aspects, the isomeric tags can comprise a functional group at a first position, a second position, a third position, a fourth position, a fifth position, a sixth position, a seventh position, etc., or a combination thereof. For example, the functional group can be an electron donating group or an electron withdrawing group. Exemplary electron donating groups include, but is not limited to $NH_2$, $OCH_3$, OH, and $CH_3$, and an electron withdrawing groups include, but are not limited to F, Cl, Br, I, $NO_2$, and CN, by way of non-limiting example. The location of the functional group can be a resonant position or a non-resonant position.

In some aspects, the isomeric tags can further comprise a location for a charge (e.g., a positive charge or a negative charge). The location for a positive charge can be, for example, a quaternary amine. For example, the quaternary amine can be an indole, a pyridine, a quinoline, an isoquinoline, or a combination thereof.

The methods described herein can include forming one or more tagged compounds, wherein each compound is tagged with a single isomeric tag. For example, a first compound is tagged with a first isomeric tag, a second compound is tagged with a second isomeric tag, a third compound is tagged with a third isomeric tag, etc. Each isomeric tag, comprising a functional group and a location for a charge, can exhibit unique behavior in a DMS. A chemical modifier, added to a transport region in the DMS, can further effect the behavior in the DMS. The DMS can effect separation of the one or more tagged compound ion complexes.

For example, these isomeric tags can be used to tag one or more compounds for detection, separation and/or quantification using DMS. In some aspects, each of the one or more tagged compound ion complexes produces a shift in a CoV value. The shift in CoV (e.g., a negative shift) can depend on the location of the functional group, the location of the charge, a chemical modifier and/or a combination thereof.

These and other features of the applicant's teaching are set forth herein.

BRIEF DESCRIPTION OF THE DRAWINGS

The skilled person in the art will understand that the drawings, described below, are for illustration purposes only. The drawings are not intended to limit the scope of the applicants' teachings in any way.

DETAILED DESCRIPTION

Figure 1:
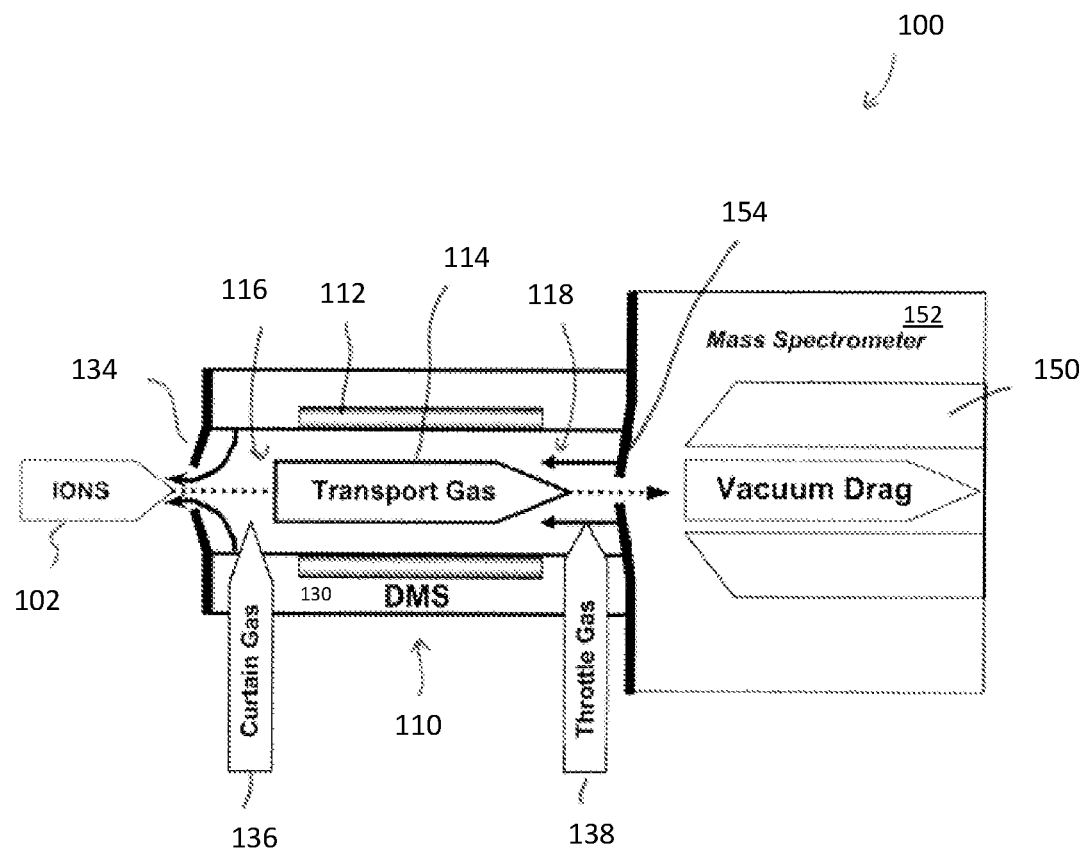
FIG. 1, in a schematic diagram, illustrates an exemplary differential mobility spectrometer/mass spectrometer system in accordance with an aspect of various embodiments of the applicants' teachings.

It will be appreciated that for clarity, the following discussion will explicate various aspects of embodiments of the applicants' teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicants' teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicants' teachings in any manner.

Methods and systems for the separation or detection of analytes (e.g., peptides, proteins, sugars, glycans, etc.) labeled with isomeric reagent tags using differential mobility spectrometry (DMS) are provided herein. Whereas typical multiplexed MS/MS workflows utilizing isotopic or isobaric labels rely on the fragmentation of the labeled analyte and release of the tags to allow for MS-based separation/detection of the unique tags, methods and systems in accordance with various aspects of the present teachings provide for the detection and/or quantification of the analytes labeled with isomeric tags that can be differentiated via a DMS upstream of a first stage mass analyzer and/or prior to fragmentation of the labeled analyte, for example. In various aspects and without being bound by any particular theory, the labeling reagents can enable separation in the DMS due to differing charge densities of the labeled analytes initiated by the atomic connectivity between the labels and the analytes. By way of example, the various connectivities of the labeling reagents with the analytes of interest can generate electronic effects (e.g., resonance effects), steric effects, the formation of intramolecular hydrogen bonds, or all within the DMS. Examples of electronic effects include, for example, the location of an electron donating or electron withdrawing group within the labeling molecule that can be effective to delocalize a charge on the labeled analyte, thereby shifting the compensation voltage of the DMS sufficiently to provide separation relative to the other labeled analytes Examples of steric effects include, for example, the blockage of a charged site within the labeled analyte, thereby altering the labeled analytes drift through the DMS during the high and/or low periods. Examples of the formation of intramolecular hydrogen bonds include, for example, the blockage of a charged site within the labeled analyte by virtue of another portion of the molecule donating electrons to the charge site in the form of an intramolecular hydrogen bond, thereby altering the labeled analytes drift through the DMS during the high and/or low periods. The differential labels described herein can include or exclude isotopes, though it will be appreciated in light of the present teachings that their exclusion can reduce the expense and/or complexity of the labeling reagents relative to reagents commonly utilized in known isotopic or isobaric tandem MS-based workflows.

Referring now to FIG. 1, an exemplary ion mobility device/mass spectrometer system 100 in accordance with various aspects of applicants' teachings is illustrated schematically. As shown in FIG. 1, the ion mobility device/mass spectrometer system 100 generally comprises a ion mobility device 110 in fluid communication with a first vacuum lens element 150 of a mass spectrometer (hereinafter generally designated mass spectrometer 150). As will be appreciated by a person skilled in the art, the ion mobility device/mass spectrometer system 100 represents only one possible configuration for use in accordance with various aspects of the systems, devices, and methods described herein.

The ion mobility device 110 can have a variety of configurations, but is generally configured to resolve ions 102 (e.g., ionized, labeled analytes) based on their mobility through a fixed or variable electric field (whereas MS analyzes ions based on their mass-to-charge ratios). It will be appreciated that though the ion mobility device 110 is commonly described herein as a differential mobility spectrometer (DMS), the ion mobility device can be any ion mobility device configured to separate ions based on their mobility through a carrier or buffer gas, including by way of non-limiting example, an ion mobility spectrometer, a drift-time ion mobility spectrometer, a traveling-wave ion mobility spectrometer, a differential mobility spectrometer (DMS), and a high-field asymmetric waveform ion mobility spectrometer (FAIMS) of various geometries such as parallel plate, curved electrode, or cylindrical FAIMS device, among others. In DMS, RF voltages, often referred to as separation voltages (SV), can be applied across the drift tube in a direction perpendicular to that of a drift gas flow. Ions of a given species tend to migrate radially away from the axis of the transport chamber by a characteristic amount during each cycle of the RF waveform due to differences in mobility during the high field and low field portions. A DC potential, commonly referred to as a compensation voltage (CV or CoV), applied to the DMS cell provides a counterbalancing electrostatic force to that of the SV. The CV can be tuned so as to preferentially prevent the drift of a species of ion of interest. Depending on the application, the CV can be set to a fixed value to pass only ion species with a particular differential mobility while the remaining species of ions drift toward the electrodes and are neutralized. Alternatively, if the CV is scanned for a fixed SV as a sample is introduced continuously into the DMS, a mobility spectrum can be produced as the DMS transmits ions of different differential mobilities.

In the exemplary embodiment depicted in FIG. 1, the differential mobility spectrometer 110 is contained within a curtain chamber 130 that is defined by a curtain plate or boundary member 134 and is supplied with a curtain gas 136 from a curtain gas supply (not shown). As shown, the exemplary differential mobility spectrometer 110 comprises a pair of opposed electrode plates 112 that surround a transport gas 114 that drifts from an inlet 116 of the differential mobility spectrometer 110 to an outlet 118 of the differential mobility spectrometer 110. The outlet 118 of the differential mobility spectrometer 110 releases the drift gas 116 into an inlet 154 of a vacuum chamber 152 containing the mass spectrometer 150. A throttle gas 138 can additionally be supplied at the outlet 118 of the differential mobility spectrometer 110 so as to modify the flow rate of transport gas 114 through the differential mobility spectrometer 110.

In accordance with certain aspects of the present teachings, the curtain gas 136 and throttle gas 114 can be set to flow rates determined by a flow controller and valves so as to alter the drift time of ions within the differential mobility spectrometer 110. Each of the curtain and throttle gas supplies can provide the same or different pure or mixed composition gas to the curtain gas chamber. By way of non-limiting example, the curtain gas can be air, $O_2$, He, $N_2$, $CO_2$, or any combinations thereof. The pressure of the curtain chamber 130 can be maintained, for example, at or near atmospheric pressure (i.e., 760 Torr). Additionally, the system 110 can include a chemical modifier supply (not shown) for supplying a chemical modifier and/or reagent to the curtain and throttle gases. As will be appreciated by a person skilled in the art, the modifier supply can be a reservoir of a solid, liquid, or gas through which the curtain gas is delivered to the curtain chamber 130. By way of example, the curtain gas can be bubbled through a liquid modifier supply. Alternatively, a modifier liquid or gas can be metered into the curtain gas, for example, through an LC pump, syringe pump, or other dispensing device for dispensing the modifier into the curtain gas at a known rate. For example, the modifier can be introduced using a pump so as to provide a selected concentration of the modifier in the curtain gas. The modifier supply can provide any modifier including, by way of non-limiting example, water, methanol, acetone, isopropanol, methylene chloride, methylene bromide, dimethyl sulfoxide, or any combination thereof.

As will be appreciated by a person skilled in the art in light of the present teachings, the chemical modifier can interact with the ionized, labeled analytes (e.g., via a charged site in the tagged compound) such that the labeled analytes differentially interact with the modifier (e.g., cluster via hydrogen or ionic bonding) during the high and low field portions of the SV, thereby effecting the CV needed to counterbalance a given SV. In some cases, this can increase the separation between analytes labeled with different labels. In various aspects and without being bound by any particular theory, the isomeric labels can modulate the separation behavior in the DMS as a result of differing charge densities of the labeled analytes due to the atomic connectivity between the isomeric labels and the analytes. Specifically, the chemical modifier can interact with the charged site (e.g., atom) in the isomeric molecules depending on the location of functional groups (e.g., electron donating group, electron withdrawing group). By way of example, the various connectivities of the isomeric labels with the analytes of interest can generate electronic effects (e.g., resonance effects), steric effects, the formation of intramolecular hydrogen bonds, or all within the DMS. Examples of electronic effects include, for example, the location of an electron donating or electron withdrawing group within the isomeric labels that can be effective to delocalize a charge on the labeled analyte, thereby shifting the CV of the DMS sufficiently to provide separation relative to analytes labeled with other isomeric labels. Examples of steric effects include, for example, the blockage of a charged site within the labeled analyte, thereby altering the labeled analytes drift through the DMS during the high and/or low portions of the SV. Examples of the formation of intramolecular hydrogen bonds include, for example, the blockage of a charged site within the labeled analyte by virtue of another portion of the molecule donating electrons to the charge site in the form of an intramolecular hydrogen bond. As further disclosed herein, the identity of the isomeric label's functional group and its location (e.g., at a resonant or a non-resonant position on the labels) can effect the interaction of a chemical modifier with the compound in the DMS, thus also effecting CV.

Ions 102 (e.g., ionized labeled analytes) can be generated by an ion source (not shown) and emitted into the curtain chamber 130 via curtain chamber inlet. As will be appreciated by a person skilled in the art, the ion source can be virtually any ion source known in the art, including for example, an electrospray ionization (ESI) source. The pressure of the curtain gases in the curtain chamber 130 (e.g., ~760 Torr) can provide both a curtain gas outflow out of curtain gas chamber inlet, as well as a curtain gas inflow into the differential mobility spectrometer 110, which inflow becomes the transport gas 114 that carries the ions 102 through the differential mobility spectrometer 110 and into the mass spectrometer 150 contained within the vacuum chamber 152, which can be maintained at a much lower pressure than the curtain chamber 130. By way of non-limiting example, the vacuum chamber 152 can be maintained at a pressure lower than that of the curtain chamber 130 (e.g., by a vacuum pump) so as to drag the transport gas 114 and ions 102 entrained therein into the inlet 154 of the mass spectrometer 150. Though not shown, the sample(s) containing the analytes of interest can be delivered to the ion source 102 from a variety of sample sources, including through direct injection, pumping from a reservoir containing a fluid sample, and via a liquid chromatography (LC) column, by way of non-limiting examples.

As will be appreciated by a person skilled in the art, the differential mobility/mass spectrometer system 100 can additionally include one or more additional mass analyzer elements downstream from vacuum chamber 152. Ions 102 can be transported through vacuum chamber 152 and through one or more additional differentially pumped vacuum stages containing one or more mass analyzer elements. For instance, in one embodiment, a triple quadrupole mass spectrometer may comprise three differentially pumped vacuum stages, including a first stage maintained at a pressure of approximately 2.3 Torr, a second stage maintained at a pressure of approximately 6 mTorr, and a third stage maintained at a pressure of approximately $10^{-5}$ Torr. The third vacuum stage can contain a detector, as well as two quadrupole mass analyzers with a collision cell located between them. It will be apparent to those skilled in the art that there may be a number of other ion optical elements in the system. Alternatively, a detector (e.g., a Faraday cup or other ion current measuring device) effective to detect the ions transmitted by the differential mobility spectrometer 110 can be disposed directly at the outlet of the differential mobility spectrometer 110. It will be apparent to those skilled in the art that the mass spectrometer employed could take the form of a quadrupole mass spectrometer, triple quadrupole mass spectrometer, time-of-flight mass spectrometer, FT-ICR mass spectrometer, or Orbitrap mass spectrometer, all by way of non-limiting example.

As discussed in detail below, the exemplary system discussed above with reference to FIG. 1 can be used to analyze and quantify one or more analytes contained within a sample or a plurality of samples in accordance with various aspects of the applicants' teachings. By way of example, methods of analyzing a plurality of samples containing (or suspected of containing) an analyte of interest are provided in which the plurality of samples can be separately reacted with the isomeric labels such that the analytes from the different samples are differentially labeled. Products of each of the separate reactions between the analytes of interest and the isomeric labels can then be mixed together, and subject to liquid chromatography, ionization, differential mobility spectrometry, mass spectrometry, or detection. For example, a labeled analyte contained within a sample can be ionized by the ion source 102, transported through the DMS 114 (e.g., with a chemical modifier present), whereby the chemical modifier interaction with the labeled analytes can effect the ion mobility separation thereof. In some aspects, the amount of interaction between the chemical modifier and the ionized labeled analyte (at a charged site), the type of functional group on the tag and the location of the functional group (e.g., at a resonant position or non-resonant position) can change or alter the compensation voltage needed at a given separation voltage. Depending on the application, the CV can be set to a fixed value to pass only labeled analytes of a particular differential mobility while the remaining species are neutralized or the CV can be scanned to iteratively select the labeled analytes of interest. In this manner, the present teachings can enable a single injection into an LC column, for example, with the differential isomeric labels enabling sufficient separation in the DMS (and possibly in conjunction with the LC separation) such that the identity of the particular sample from which the analyte originated and/or the quantity of the analyte in that sample can be determined. By using a single sample injection to analyze the results across the plurality of labelling reactions, methods in accordance with various aspects of the present teachings can provide for increased throughput and decreased complexity and variability (e.g., between runs).

Isomeric labels in accordance with the present teachings can comprise a variety of chemical compounds that can be reacted with the analyte of interest so as to generate a labeled analyte, wherein the differences in the chemical structures of the various labels result in different differential ion mobility behaviors. Generally, sets of isomeric labels for use in accordance with the present teachings comprise families of isomers exhibiting identical chemical formulas but of differing chemical structures such that when bound to the analyte of interest, the differentially labeled analytes exhibit differential ion mobilities that can be resolved by modulating the conditions of the ion mobility spectrometer. By way of example, the isomeric labels can comprise one or more functional groups (e.g., electron donating group and/or electron withdrawing group) disposed at different locations of a compound (e.g., a resonant or non-resonant position) such that electronic effects (e.g., resonance effects), steric effects, the formation of intramolecular hydrogen bonds, or all result in the DMS.

Figure 2A:
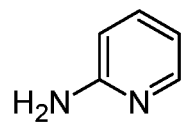
FIGS. 2A-C illustrate the chemical structures of three aminopyridines (2-AP, 3-AP, and 4-AP) for use as exemplary labels in accordance with various aspects of the applicants' teachings.
Figure 2B:
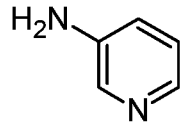
Figure 2C:
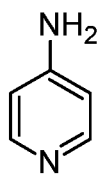

With reference now to FIGS. 2A-C, an exemplary set of isomeric labels in accordance with various aspects of the present teachings is depicted. As shown, the labels comprise three isomeric aminopyridines (2-AP, 3-AP and 4-AP) in which the amine group ($-NH_2$) is located at various positions of the pyridine ring. Though 2-aminopyridine (2-AP) is commonly utilized in fluorescence and capillary electrophoresis labeling, 3-Aminopyridine (3-AP) and 4-Aminopyridine (4-AP) are not typically used for tagging and labeling due to their decreased fluorescence. However, in accordance with the present teachings, after reacting these isomeric labels with an analyte of interest, the analyte-aminopyridine complexes can be sufficiently resolved from one another via DMS to allow for their differential detection.

Figure 3:
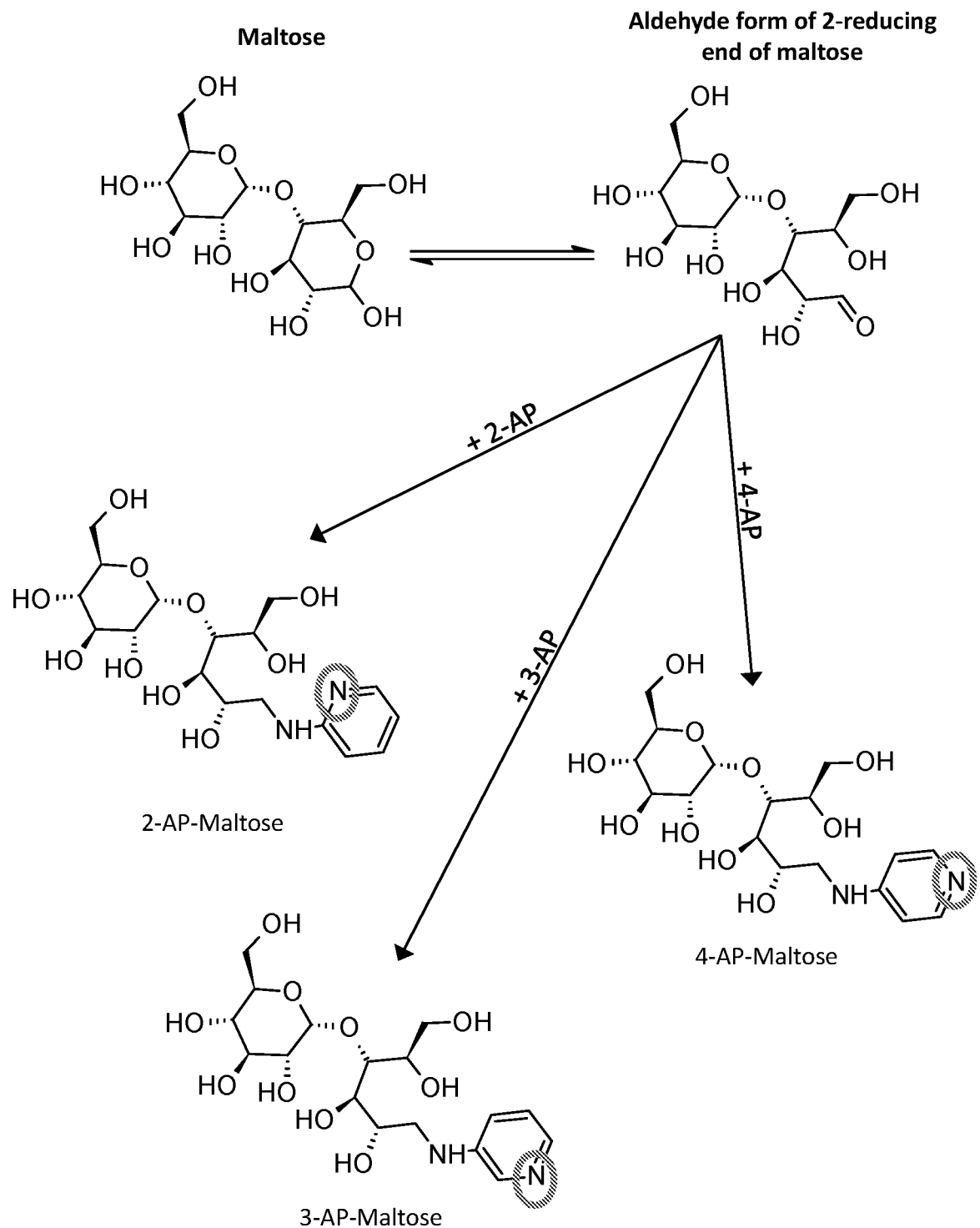
FIG. 3 illustrates an exemplary reaction scheme for labeling maltose with the labels of FIGS. 2A-C.

With reference now to FIG. 3, one exemplary reaction scheme is depicted for labeling an exemplary glycan representing an analyte of interest (i.e., maltose) with the isomeric aminopyridine labels of FIGS. 2A-C, thereby generating 2-AP-Maltose, 3-AP-Maltose, and 4-AP-Maltose. As a specific example, maltose is reacted with a mixture of one of the 2-AP, 3-AP, and 4-AP labels, DMSO, acetic acid, and sodium cyanoborohydride to form one of 2-AP-Maltose, 3-AP-Maltose, and 4-AP-Maltose, respectively. In some aspects, the sample can be cleaned to remove free 2-AP, 3-AP, and 4-AP prior to delivering the sample to an ion source for ionization and subsequent DMS analysis. Additionally, as noted above, multiple samples, each containing differentially labeled maltoses can be combined for a single delivery to the LC and/or ion source.

Figure 4:
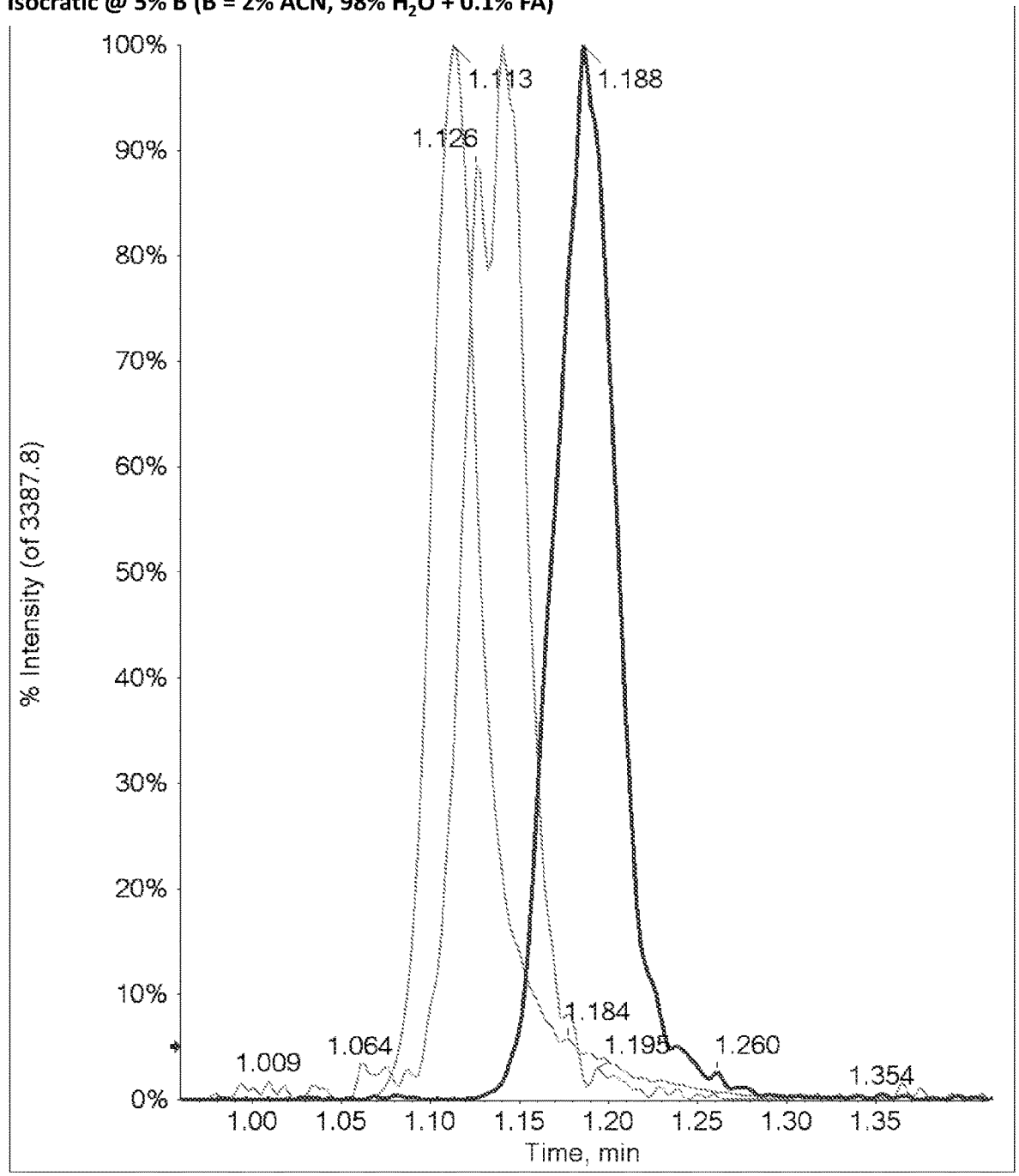
FIG. 4 illustrates LC elution of maltose labeled with the labels of FIGS. 2A-C at 5% concentration of the mobile phase (2% acetonitrile, 98% $H_2O$ and 0.1% formic acid) under isocratic conditions.

With reference now to FIG. 4, this plot illustrates LC elution of 2-AP, 3-AP, and 4-AP labeled maltose at a 5% concentration of the mobile phase (2% acetonitrile, 98% $H_2O$ and 0.1% formic acid) under isocratic conditions. 2-AP-maltose is the trace labelled 1.188, 3-AP-maltose is the leftmost trace labelled 1.113, and 4-AP-maltose is the middle trace containing the peak labelled at 1.126. As shown in this study, of the various exemplary LC conditions tested, the 2-AP, 3-AP, and 4-AP-labeled analytes were best resolved in the C18 reverse phase column operating under isocratic conditions with a mobile phase comprising a 5% solution of 2% acetonitrile, 98% $H_2O$, and 0.1% formic acid (FIG. 4). It will be appreciated by a person skilled in the art therefore that it is within the scope of the present teachings that the LC conditions can thus be optimized for particular analytes labeled in accordance with the teachings herein. Moreover, though the depicted LC conditions utilize an isocratic elution with a given mobile phase, it will be appreciated that these are mere examples and that LC can be performed with a gradient elution of any known mobile phase so as to provide additional separation of the samples prior to DMS.

Elution and Separation of 2-AP, 3-AP and 4-AP Labeled Maltose Using DMS

Figure 5:
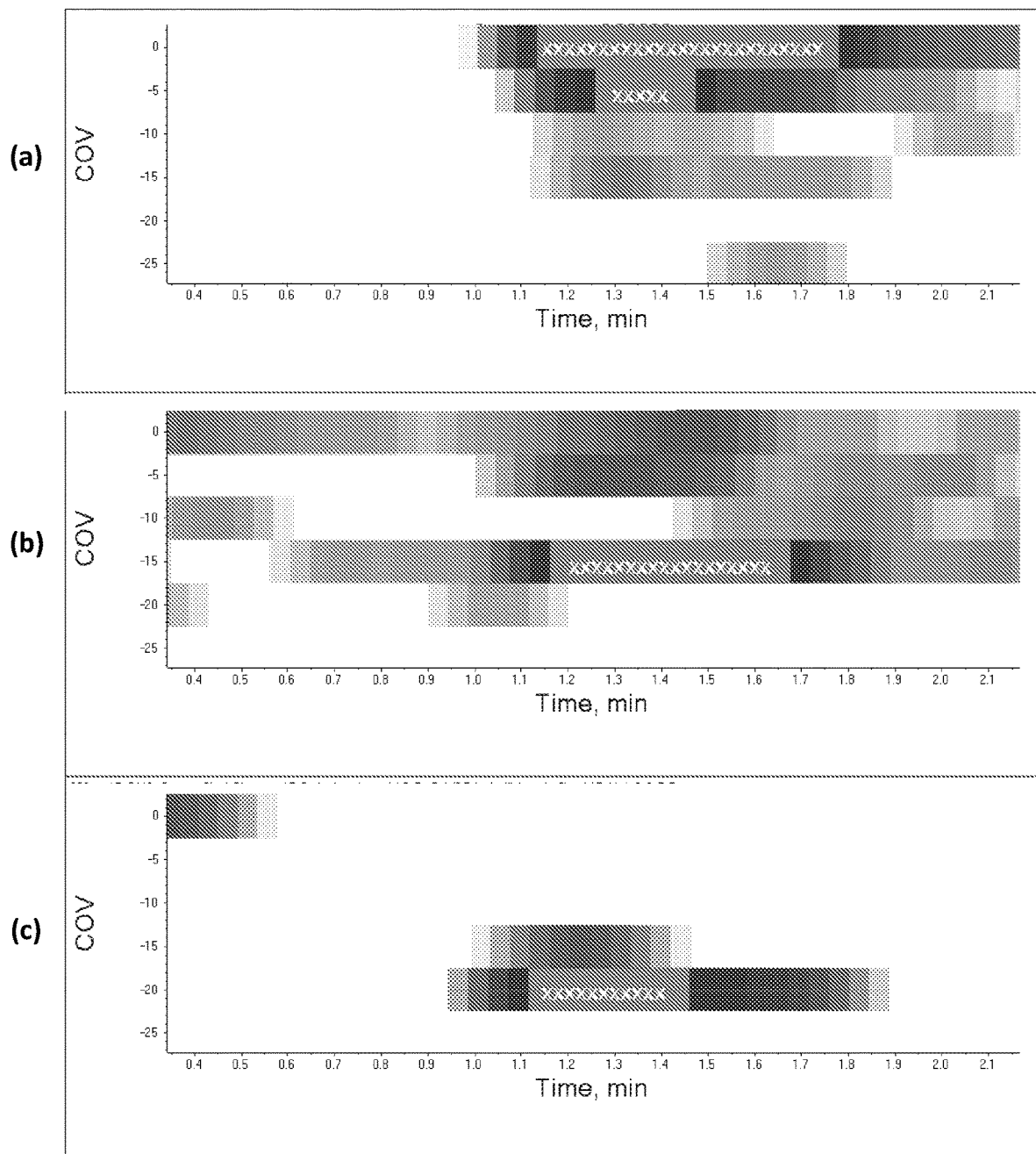
FIG. 5 illustrates exemplary heat maps corresponding to the intensity of the MS signal at various CoV and elution times during the LC elution depicted in FIG. 5C.

With reference now to FIG. 5, exemplary heat maps are depicted corresponding to the intensity of the MS signal at various elution times during the LC elution depicted in FIG. 5C, with the DMS in operating mode. The most intense part of the heat maps are marked by x's. As noted above, the DMS in these tests was performed using a SelexIon DMS system coupled to a SCIEX 5600+ quadrupole time-of-flight mass spectrometer with the SV being set at 4000V, isopropyl alcohol (IPA) as the DMS chemical modifier liquid and the CV being ramped as indicated in the figure. Specifically, the heat map depicted in FIG. 5(a) represents the detected intensity of ions in the sample containing 2-AP-Maltose at various elution times and at various CV along the trace having a peak at 1.188 of FIG. 4, the sample containing 3-AP-Maltose at various elution times and at various CV along the trace having peak at 1.126 of FIG. 4, and the sample containing 4-AP-Maltose at various elution times and at various CV along the trace having a peak at 1.113 of FIG. 4. As illustrated, 4-AP-maltose had the largest negative CoV shift at its peak intensity (FIG. 5(c), at about −20V DC between about 1.1 and 1.5 minutes), while 3-AP-maltose (FIG. 5(b), about −15V DC between about 1.2 and 1.7 minutes) exhibited a slightly smaller negative shift relative to the CoV at peak intensity of the 2-AP labeled maltose (FIG. 5(a), about 0 to −5V DC between about 1.2 and 1.8 minutes).

It will thus be appreciated as illustrated by FIG. 5, that substituted isomeric aminopyridines at the 2, 3, or 4 position can allow for the identification (detection), separation and quantification of glycans (e.g., maltose) using LC in combination with DMS, example. Without being bound by any particular theory, it is believed that tagging maltose at the 2, 3, or 4 position of aminopyridine effects the interaction between the ring nitrogen (circled in FIG. 3 with the chemical modifier (e.g., isopropyl alcohol) and the labeled analytes are transmitted through the DMS. For example, when the amine group (—$NH_2$) is at the 4-position of the pyridine ring as in the 4-AP label, it is believed that the ring nitrogen may more freely interact with a chemical modifier in the DMS, thereby resulting in the large negative shift in the compensation voltage. Likewise, substitution of the amine group at the 3 position and 2 position can result in different differential mobility behavior (e.g., through the interaction of the ring nitrogen and the chemical modifier), through steric effects such as physical blockage of the ring nitrogen by the maltose molecule or the formation of intra-molecular hydrogen bonds between the AP group and adjacent hydroxyl groups on the maltose molecule. Thus, it will be appreciated that shifts in compensation voltages for a set of isomeric tags having different substitutions (e.g., 2-AP, 3-AP, and 4-AP) can allow for selective transmittal of the labeled analyte of interest through the DMS, and subsequently, the detection and/or quantification of these labeled analytes.

Figure 6A:
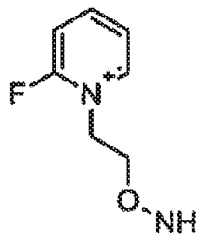
FIGS. 6A-C illustrate the chemical structures of three fluorine-substituted N-alkyl-pyridinium compounds for use as exemplary labels in accordance with various aspects of the applicants' teachings.
Figure 6B:
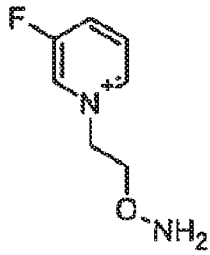
Figure 6C:
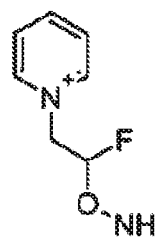

With reference now to FIGS. 6A-C, another exemplary set of isomeric labels in accordance with various aspects of the present teachings is depicted. As shown, the labels comprise three isomeric fluorine-substituted N-alkyl-pyridinium compounds. Specifically, FIG. 6A shows the chemical structure of 2-fluoro-N-alkyl-pyridinium (i.e., 1-(2-(aminooxy)ethyl)-2-fluoropyridin-1-ium), FIG. 6B shows the chemical structure of 3-fluoro-N-alkyl-pyridinium (i.e., 1-(2-(aminooxy)ethyl)-3-fluoropyridin-1-ium), and FIG. 6C shows the chemical structure of N-fluoroalkyl-pyridinium (i.e., 1-(2-(aminooxy)-2-fluoroethyl)pyridin-1-ium). Like the exemplary labels of FIGS. 2A-C, the labels of FIGS. 6A-C comprise a pyridine ring, but instead comprise a fluorine atom substituted at the 2- and 3-position (6A and 6B, respectively) and an isomeric label in which the fluorine is not connected directly to the pyridine ring (6C). Additionally, these exemplary labels differ relative to those of FIGS. 3A-C in that they include an aminooxy group (as opposed to an amine group). Nonetheless, like the isomeric labels of FIG. 3A-C, the fluorine-substituted N-alkyl-pyridinium compounds can be reacted with an analyte of interest in accordance with the present teachings so as to generate labeled analytes that can be sufficiently resolved from one another via DMS to allow for their differential detection. In some aspects, the fluorine can be substituted with other functional groups as described herein. In this example, however, a fluorine functional group at the 2 position (FIG. 6A) is in resonance with the pyridine ring such that the fluorine atom can partially donate electrons to the π-system of the pyridinium, to offset the positive charge, which results in a large negative CV shift in the DMS. When the fluorine is moved to a non-resonant position as shown in FIG. 6B, a moderate negative shift in CV is observed. Finally, when fluorine is not part of the π-system as shown in FIG. 6C, no influence on the charge site from resonance interactions should occur and little to no shift in CV should occur.

Though fluorine is depicted as the substituent in the exemplary isomeric labels of FIGS. 6A-C, it will be appreciated that any number of functional groups can be utilized in accordance with the present teachings. For example, with reference now to FIGS. 7A-C, another exemplary set of potential isomeric labels in accordance with various aspects of the present teachings is depicted. As shown, each isomeric set of these labels comprise three substituted 2-methyl-quinolin-8-ol compounds, with the functional group (—X) being substituted at various positions of the quinolone ring, wherein the functional group can be any of $OCH_3$, $CH_3$, F, Br, or CN, by way of non-limiting example. Specifically, FIG. 7A shows the chemical structure of a substituted 2-methyl-quinolin-8-ol at the 5-position, FIG.

Figure 7A:
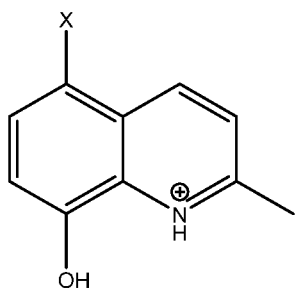
FIGS. 7A-C illustrate the chemical structures of three exemplary substituted 2-methyl-quinolin-8-ol compounds for use as exemplary labels in accordance with various aspects of the applicants' teachings.
Figure 7B:
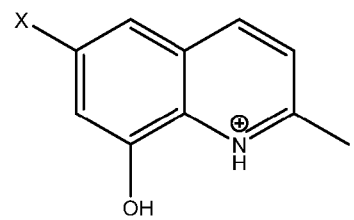
Figure 7C:
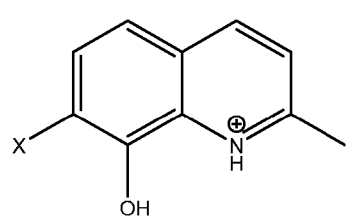
Figure 8A:
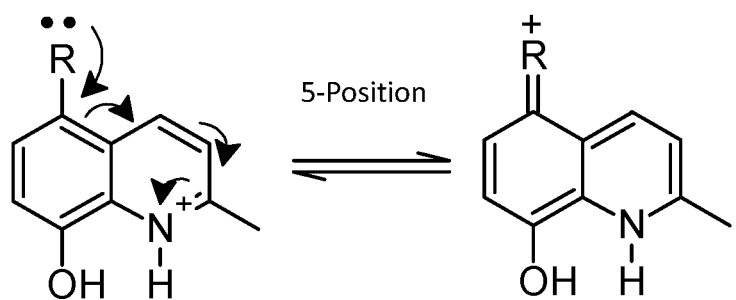
FIGS. 8A-C illustrate the resonance effect of an electron donating (R) group at positions of the methyl-quinolin-8-ols of FIGS. 7A-8C, respectively.
Figure 8B:
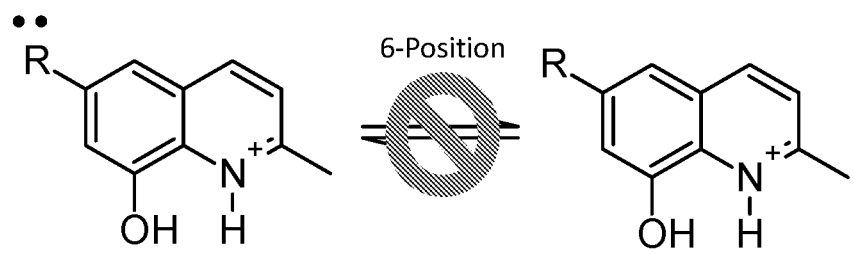
Figure 8C:
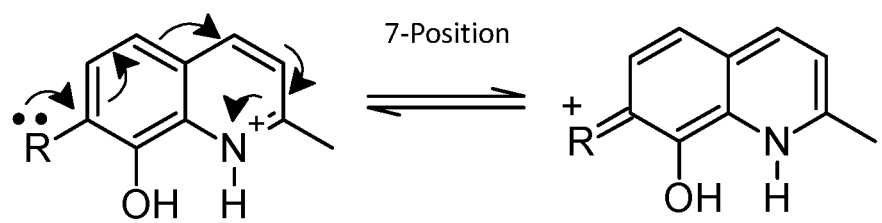

7B shows the chemical structure of a substituted 2-methyl-quinolin-8-ol at the 6-position, and FIG. 7C shows the chemical structure of a substituted 2-methyl-quinolin-8-ol at the 7-position. The labels illustrated in FIGS. 7A-C also have a location for a charged site or atom, i.e., the protonated nitrogen in the quinoline. Thus, the functional group (—X) in FIGS. 7A and 7C is in a resonant position such that electrons from an electron donating functional group can be added into the ring system of p orbital-electrons. For example, as illustrated in FIGS. 8A and 8C, a functional group (e.g., an electron donating group) at the 5- or 7-position, can donate electrons to the π-conjugated system as these substituents are capable of interacting with the site of ion charging via resonance. A functional group at the 6 position (FIG. 7B), however, is not in resonance and cannot donate electrons to the site of charging via the π-conjugated system (FIG. 8B).

Based upon related data acquired for a set of substituted quinoline ions shown in FIGS. 7A-C, it was observed that with an electron-donating group (EDG) at a resonant position, electron density was donated to the positive charge at the ring nitrogen. Since the overall charge of the ion was made more diffuse, these ions exhibited weaker interactions with the chemical modifiers in the DMS cell and concomitantly less negative CV shifts are observed. However, when the electron donating group was at a non-resonant position, less weakening of the ion/chemical modifier interaction was observed. That is, a shift to the left (i.e., more negative) in the CoV values was observed. The species of the differentially labeled analytes were thus separated in the DMS based upon the electronic interactions between the charged site and functional groups in the isomeric label. Without being bound to any particular theory, it is believed that the association of a functional group as described herein (e.g., electron withdrawing group or electron donating group) within the label can effect the transmission of the labeled analyte through the DMS due to differing interactions with modifier molecules within the carrier gas, thereby resulting in shifts in CV. For example, as illustrated in FIGS. 8A-C, an electron-donating functional group ("R") at a resonant position can help stabilize and delocalize the positive charge. An electron donating group (EDG) can donate some of its electron density into the conjugated π system via resonance. For example an EDG at the 5-position (FIG. 8A) and 7-position (FIG. 8C) can be in equilibrium between a charged and uncharged amine. However, an electron donating group at a non-resonant position (FIG. 8B) cannot delocalize the charge on the amine, thereby differentially effecting the optimum CV for each of these compounds due to this electronic effects.

It has thus been discovered that certain isomeric molecules exhibit different characteristics in a DMS. Specifically, isomeric labels in accordance with various aspects of the present teachings can have a functional group at certain positions such that the differentially labeled analytes exhibit unique characteristics in a DMS. The isomeric labels and their functional groups described herein, can provide electronic effects (e.g., resonance effects), steric effects, the formation of intramolecular hydrogen bonds, or all to the isomeric label. Examples of electronic effects are described herein, and can include electron donating or electron withdrawing groups in a pi-conjugated system with can, for example, effect a charged site or atom. For example, an electron donating functional group in resonance can contribute electrons to a pi-system to delocalize a positive charge.

For example, in some embodiments, the functional group can be an electron-donating group. Electron donating groups can contribute to electron density within a molecule. That is, electron donating groups can add electron density to a π system via resonance. Electron donating groups include, but are not limited to, $NH_2$, $OCH_3$, OH, and $CH_3$. The electron donating group can be at a resonant position or a non-resonant position in the tag.

Alternatively, in some aspects, the labels comprise one or more electron withdrawing groups (EWG) at one or more positions. For example, in some embodiments, the functional group can be an electron withdrawing group that can delocalize electrons within a molecule. That is, electron withdrawing groups can remove electron density from a π system via resonance. For example, the electron-withdrawing groups includes, but are not limited to, F, Cl, Br, I, $NO_2$, and CN. The electron withdrawing group can be at a resonant position or a non-resonant position in the tag.

In some embodiments, the functional group can additionally or alternatively provide steric effects to the isomeric label. For example, the functional group can partially or completely block (e.g. physically block) a chemical modifier from interacting with a charged site in the label. For example, a large functional group can provide steric effects so that a chemical modifier in the DMS cannot interact with (e.g., via hydrogen bonding) with a charged site on the isomeric label. The more hindered a charged site from large functional groups, the weaker the binding with a chemical modifier, which can in some aspects result in a less negative CV shift in a DMS.

In some embodiments, the functional group can additionally or alternatively be involved in intramolecular hydrogen bonding (IMHB) with the ion's charge site on one species of the isomeric label, while it will not be involved in IMHB on another species of the isomeric label. Isomers engaged in IMHB will typically observe lesser degrees of interaction with solvent molecules in a DMS cell compared to non-IMHB isomers, hence the driving force for their separation. Again, the more hindered a charged site from large functional groups, the weaker the binding with a chemical modifier, which can in some aspects result in a less negative CV shift in a DMS.

In some embodiments, the isomeric tags can comprise a charged site or atom (e.g., a protonated or deprotonated site). For example, FIGS. 6A-C each show a positive charge on the pyridine ring nitrogen. Similarly, FIGS. 7A-C show a positive charge on the quinoline nitrogen. Other amine-containing isomeric tags can also be the site of a charge. Primary, secondary and tertiary amines can, for example, be protonated. Quaternary amines are positively charged, and can be also a site for a charge. A charged atom or site within an isomeric tag can be accomplished in other ways known to one of ordinary skill in the art. For example, protonation or deprotonation at a particular site can create a charge at that site. The formation of other bonds, such as covalent bonds can have the same effect. In some embodiments, the charged site can be permanently charged. In some embodiments, the charged site can be charged only under certain conditions (e.g., pH, temperature, etc.).

In some embodiments, the isomeric tag can also have a chemically reactive moiety so as to tag (e.g., form a covalent bond with) a compound. The chemically reactive moiety can react with the compound forming a covalent bond between the moiety and the compound. In some embodiments, the chemically reactive moiety can be at or near a location of a charged atom. For example, the chemically reactive moiety can comprise a quaternary amine, such as an indole, a pyridine, a quinoline, an isoquinoline, or a combination thereof.

Examples

As shown in FIGS. 9 and 10, exemplary data demonstrating the effect on CoV of the various exemplary isomeric labels described above with reference to FIGS. 8A-C, as well as differences in the separation of labeled analytes result from the effect of different modifiers is provided.

Figure 9A:
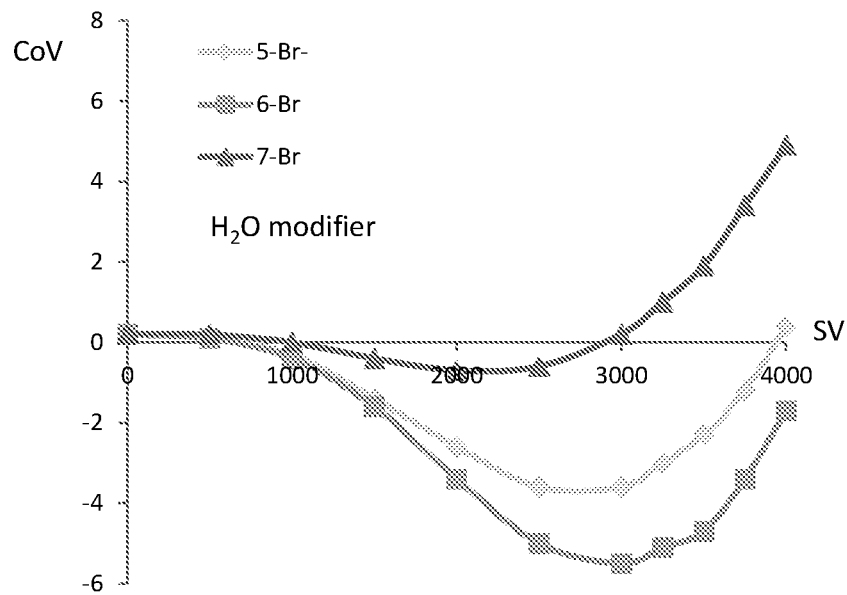
FIGS. 9A and 9B depict exemplary CoV/SV curves for the 2-methyl-quinolin-8-ols depicted in FIG. 7A-C as transmitted by a differential mobility spectrometer (with $H_2O$ as a modifier).
Figure 9B:
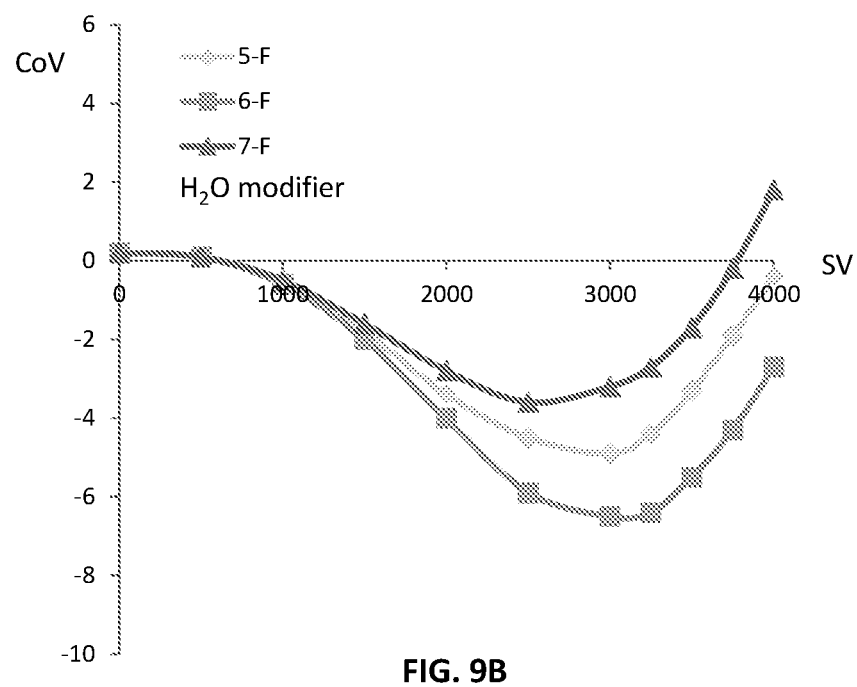

With reference first to FIGS. 9A and 9B, exemplary CoV/SV curves for the 2-methyl-quinolin-8-ols depicted in FIG. 7A-C as transmitted by a differential mobility spectrometer (with water as the modifier) are provided. The use of water as the modifier resulted in a negative shift of the CoV and improved the DMS separation for each functional group (i.e., F or Br), with maximum separation occurring at various CoV/SV settings, with SV voltages of about 2500 to about 4000 volts, demonstrating varying separation between the functional group substitutions at the 5-, 6-, and 7-positions due to resonance effects and the electronic nature of the individual substituents.

The observed shifts in compensation voltage were greatest when an electron-withdrawing group (EWG) was at a resonant position (i.e., in resonance) with a charged site. Also, the use of a chemical modifier (e.g., water or methanol) binding increased shifts of the compensation voltage. Further, the stronger the binding of the isomeric compound (at the charged site) with the chemical modifier the more negative CV shifts were observed. This effect was mitigated when the EWG was located in a position where resonance was not a factor.

Figure 10A:
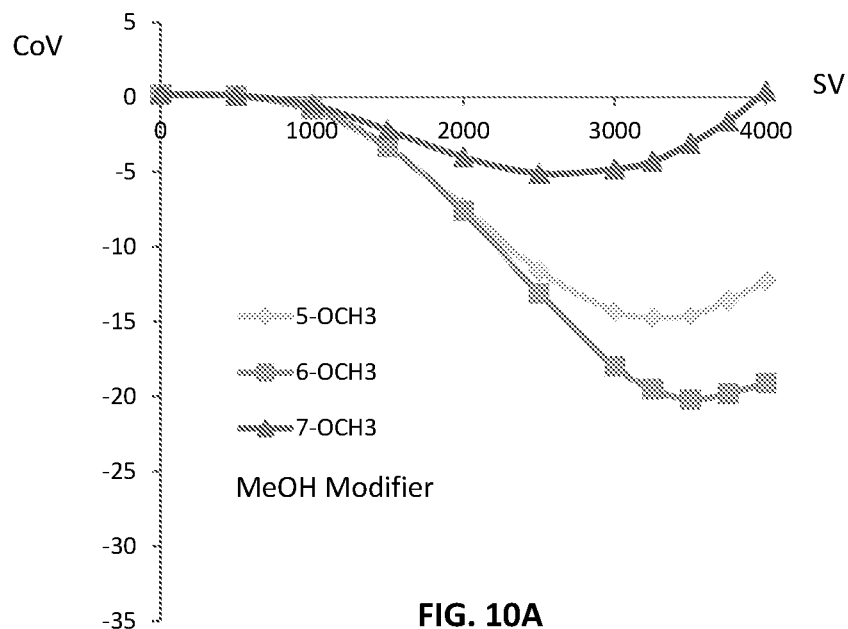
FIGS. 10A and 10B depict exemplary CoV/SV curves for the 2-methyl-quinolin-8-ols depicted in FIG. 7A-C as transmitted by a differential mobility spectrometer (with MeOH as a modifier).
Figure 10B:
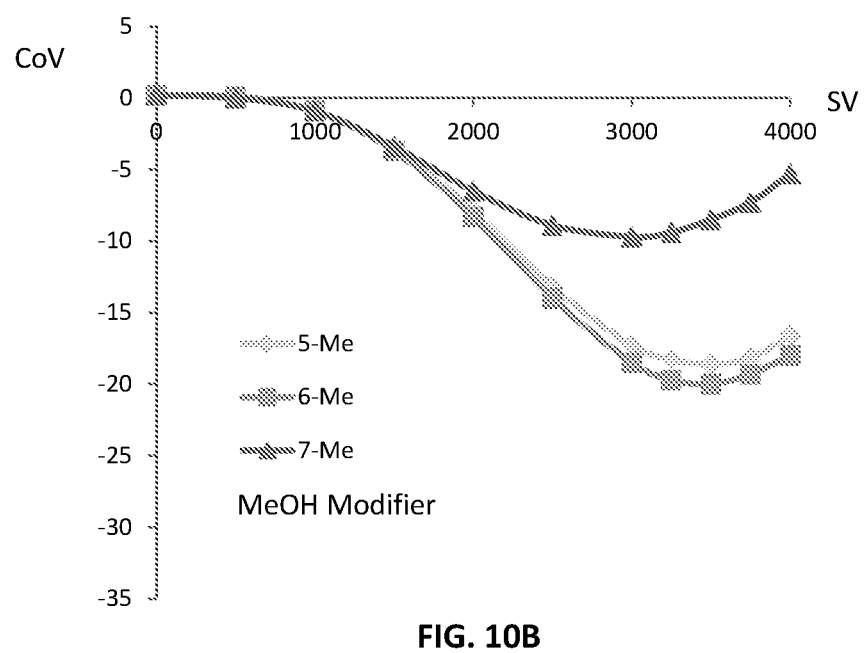

FIGS. 10A and 10B, exemplary CoV/SV curves for the 2-methyl-quinolin-8-ols depicted in FIG. 7A-C as transmitted by a differential mobility spectrometer (with methanol as the modifier) are provided. The use of methanol as the modifier resulted in a negative shift of the CoV and improved the DMS separation for each functional group (i.e., $CH_3$, $OCH_3$), with maximum separation occurring at various CoV/SV settings, with SV voltages of about 2500 to about 4000 volts, demonstrating varying separation between the functional group substitutions at the 5-, 6-, and 7-positions due to resonance effects and the electronic nature of the individual substituents.

The observed shifts in compensation voltage were greater when methanol was employed as a chemical modifier than water because of the greater binding energy of these ion/methanol clusters. In addition, the CV shifts for the $CH_3$-modified ions were more negative than for the $OCH_3$-modifier analogues. This is due to the fact that $OCH_3$ can donate more electron density to the quinoline ring as an electron donating group (EDG) thereby providing weaker binding of the isomeric compound (at the charged site) with the chemical modifier the compared to $CH_3$. Again, this effect was mitigated when the EDG was located in a position where resonance was not a factor.

Figure 11:
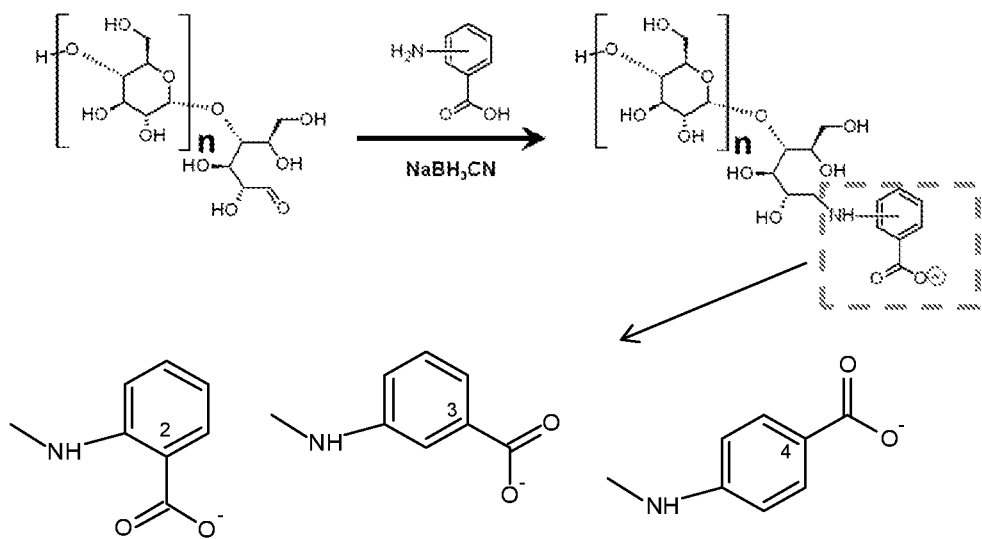
FIG. 11 depicts an exemplary labelling reaction of a glycan with various isomers of aminobenzoic acid.

FIGS. 11-14 depicts an exemplary method of labelling that utilizes difference in the substitution patterns that allows differences in intramolecular hydrogen bonding to be utilized to effect ion mobility separation. FIG. 11 depicts the labelling process of glycan type structures with various isomers of aminobenzoic acid wherein the carboxylic acid group is substituted at the 2, 3 and 4 positions of the aromatic ring structure.

Figure 12:
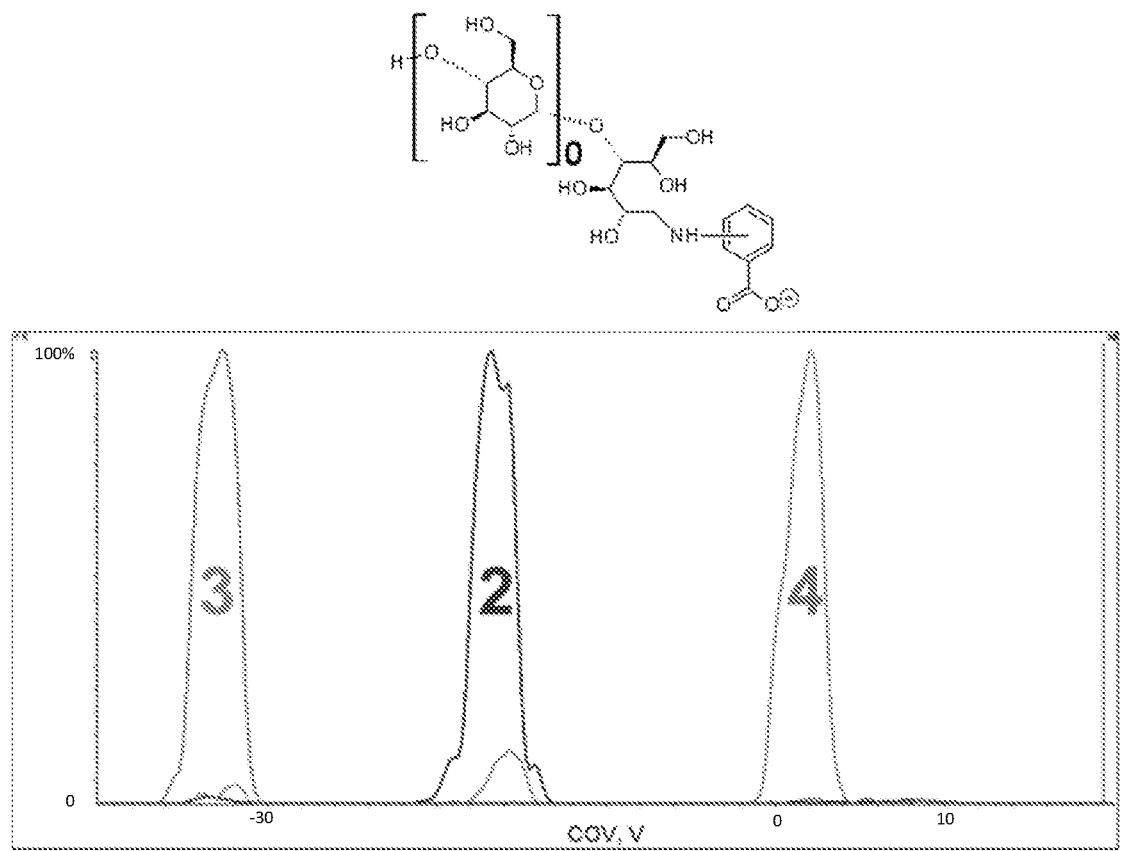
FIG. 12 depicts DMS ionograms of glucose labelled with various isomers of aminobenzoic acid.

FIG. 12 depicts the structure of an aminobenzoic acid labeled glucose molecule along with a DMS ionogram. Each main peak has been labelled with the positional isomer of aminobenzoic acid that was used in the labeling to generate the ionogram. (eg, the peak labelled "2" represents the ionogram of glucose labelled with 2-aminobenzoic acid, "3" is glucose labelled with 3-aminobenzoic acid, etc.). The ionogram demonstrates that glucose labelled with the 2-, 3-, and 4-positional isomers of aminobenzoic acid can be adequately separated in a DMS from the other isomers.

Figure 13:
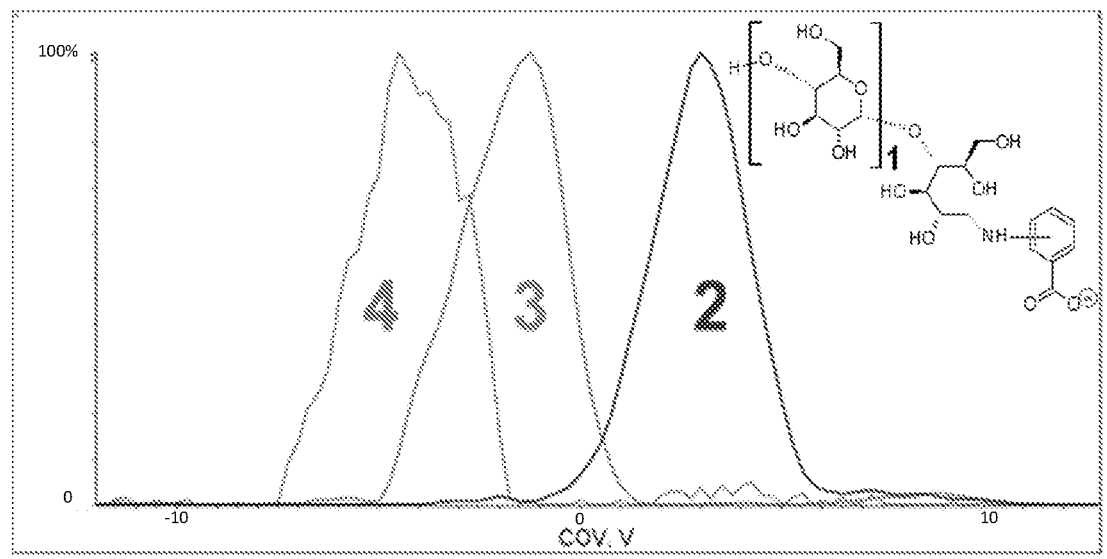
FIG. 13 depicts DMS ionograms of maltose labelled with various isomers of aminobenzoic acid.

FIG. 13 depicts the structure of an aminobenzoic acid labeled maltose molecule along with a DMS ionogram of various isomers. The ionogram demonstrates that maltose labelled with the 2-, 3- and 4-positional isomers of aminobenzoic acid can be adequately separated in a DMS from the other isomers.

Figure 14:
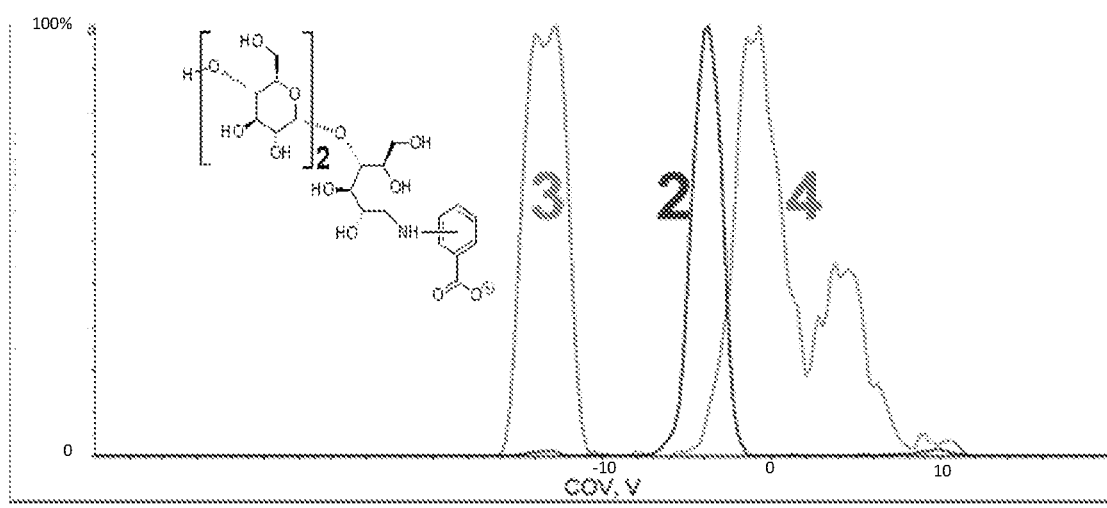
FIG. 14 depicts a DMS ionograms of maltotriose labelled with various isomers of aminobenzoic acid.

FIG. 14 depicts the structure of an aminobenzoic acid labeled maltotriose molecule along with a DMS ionogram of various isomers. The ionogram demonstrates that maltotriose labelled with the 2-, 3- and 4-positional isomers of aminobenzoic acid can be adequately separated in a DMS from the other isomers.

In light of this exemplary data, it will be appreciated by a person skilled in the art therefore that the DMS conditions (and the selection of a modifier) can thus be optimized to maximize separation of the isomeric-labeled analytes in accordance with the teachings herein.

The above examples and data demonstrate the separation of analytes labeled with isomeric labels using differential mobility spectrometry in accordance with various aspects of the teachings herein. Likewise, it has been shown that tagging compounds with isomeric labels can enable their detection, separation, and quantification using DMS through effecting the shift in compensation voltage by varying the location (e.g., position) of a functional group and the use of a chemical modifier. Resonance and/or steric interactions are also shown to effect the interaction between a charged site on the labeled analyte and a chemical modifier, thus causing a change in behavior in a DMS. Other embodiments of the applicant's teachings will be apparent to those skilled in the art from consideration of the present specification and practice of the present teachings disclosed herein. It is intended that the above examples be considered as exemplary only.

The section headings used herein are for organizational purposes only and are not to be construed as limiting. While the applicants' teachings are described in conjunction with various embodiments, it is not intended that the applicants' teachings be limited to such embodiments. On the contrary, the applicants' teachings encompass various alternatives, modifications, and equivalents, as will be appreciated by those of skill in the art.

What is claimed:

1. A method of analyzing a plurality of samples, comprising:

separately reacting first and second samples containing or suspected of containing an analyte of with different isomeric labels so as to differentially label the analytes from each sample, thereby generating a plurality of differentially labeled analytes, wherein the different isomeric labels are different in the locations of binding of a functional group, wherein the functional group is at a resonant position on one species of the isomeric label and at a non-resonant position on another species of the isomeric label;

mixing the differentially labeled analytes;

ionizing the mixture of differentially labeled analytes so as to generate ionized labeled analytes; and performing ion mobility spectrometry on the ionized labeled analytes.

2. The method of claim 1, further comprising performing liquid chromatography on the mixture of differentially labeled analytes prior to performing ion mobility spectrometry.

3. The method of claim 1, wherein the ion mobility spectrometry is performed with a differential mobility spectrometer and wherein the method further comprises adjusting at least one of a compensation voltage and a separation voltage of the differential mobility spectrometer to maximize transmission therethrough of one species of the ionized labeled analytes relative other species of the ionized labeled analytes.

4. The method of claim 1, further comprising adding a chemical modifier to a carrier gas of the ion mobility spectrometer to maximize transmission therethrough of one species of the ionized labeled analytes relative other species of the ionized labeled analytes.

5. The method of claim 1, wherein the functional group is an electron donating group selected from the group consisting of $NH_2$, $OCH_3$, OH, and $CH_3$ or an electron withdrawing group selected from the group consisting of F, Cl, Br, I, NO2, and CN.

6. The method of claim 1 wherein the different isomeric labels are fluorine-substituted N-alkyl-pyridinium compounds or substituted 2-methyl-quinolin-8-ols compounds.

* * * * *